United States Patent
Bloomer et al.

(10) Patent No.: US 6,762,034 B1
(45) Date of Patent: Jul. 13, 2004

(54) RESORUFIN DERIVATIVES AS SUBSTRATES FOR CYP3A4

(75) Inventors: Jacqueline Carol Bloomer, Welwyn (GB); Richard Leonard Elliott, Harlow (GB); Colin Andrew Leach, Harlow (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 09/890,009

(22) PCT Filed: Jan. 13, 2000

(86) PCT No.: PCT/EP00/00297

§ 371 (c)(1),
(2), (4) Date: Jan. 2, 2002

(87) PCT Pub. No.: WO00/44933

PCT Pub. Date: Aug. 3, 2000

(30) Foreign Application Priority Data

Jan. 29, 1999 (GB) ............................................. 9902068

(51) Int. Cl.[7] .................................................. C12Q 1/26
(52) U.S. Cl. ........................................ 435/25; 544/111
(58) Field of Search ............................ 435/25; 544/111

(56) References Cited

U.S. PATENT DOCUMENTS 4,954,630 A * 9/1990 Klein et al. .................. 544/102
6,143,492 A * 11/2000 Makings et al. ............... 435/4

OTHER PUBLICATIONS

Crespi, C. L., et al. "*Microtiter Plate Assays for Inhibition of Human Drug–Metabolizing Cytocromes P450*" Analytical Biochemistry, U.S. Academic Press, vol. 248, 1997, pp. 188–190 (XP002115753).

Kenworthy, K.E., Bloomer, J.C., Clarke, S.E., Houston, J.B., "*CYP3A4 Drug Interactions: Correlation of 10 in vitro probe substrates*", British Journal of Clinical Pharmacology, vol. 48, Nov. 1, 1999, pp. 716–727 (XP000921042).

Ono, S., Hatanaka, H. et al., "*Specificity for substate and inhibitor probes for cytochrome P450s: evaluation of in vitro metabolism using cDNA–expressed human P450s and human liver microsomes*", XENOBIOTICA, vol. 26, No. 7, 1996, pp. 681–693 (XP000921045).

* cited by examiner

Primary Examiner—Sandra E. Saucier
(74) Attorney, Agent, or Firm—Nora Stein-Fernandez; Theodore R. Furman

(57) ABSTRACT

Resorufin derivative as a substance for cytochrome P450 enzyme.

6 Claims, 1 Drawing Sheet

Figure 1: <u>Inhibition of resorufin 3-(4-phenylpiperazin-1-yl)methylbenzyl ether metabolism with ketoconazole</u>
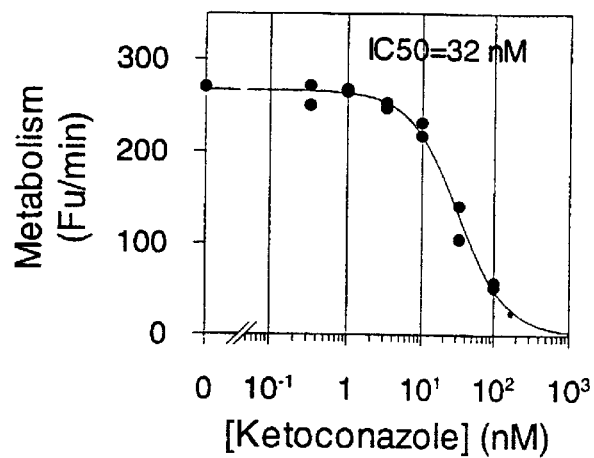

RESORUFIN DERIVATIVES AS SUBSTRATES FOR CYP3A4

This invention relates to compounds, processes for preparing them and their use as enzyme substrates.

The majority of metabolism based drug interactions are a result of inhibition of cytochrome P450 enzymes. Drug interactions involving individual P450 enzymes can be predicted using in vitro methods. Typical in vitro P450 enzyme assays involve incubation of an appropriate substrate with a source of enzyme. Traditionally, time consuming chromatographic methods have been used for metabolite detection in these incubations. More recently the availability of fluorimetric plate readers has facilitated the higher throughput of enzyme assays in general. Adapting P450 assays to fluorescent plate reader technology requires the identification of substrates with appropriate fluorescent products for individual enzymes. Among the xenobiotic-metabolising cytochromes P450, CYP3A4 is one of those commonly responsible for the metabolism of drugs.

Resorufin benzyl ether has been described for high throughput CYP3A4 inhibition screening (Crespi et al, *Anal. Biochem.*, 1997, 248, 188–190). However, the rate of Resorufin benzyl ether metabolism by CYP3A4 is low, therefore a more appropriate CYP3A4 substrate is required to enable higher throughput inhibition screening.

A compound has now been identified which is an improved substrate for CYP3A4 and which is of use for configuring high throughput inhibition screening assays.

According to the present invention there is provided an assay for testing for inhibitors of the enzyme CYP3A4 which comprises contacting the enzyme and a compound of formula (I):

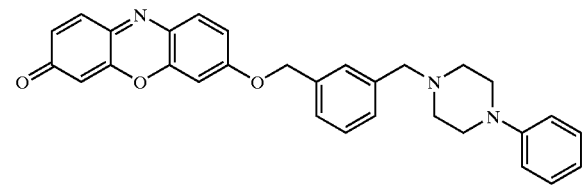

with a test compound and measuring inhibition of O-dealkylation of the compound of formula (I) by the enzyme.

Generally the rate of O-dealkylation of the compound of formula (I) in the absence of test compound will be known, as will the extent of O-dealkylation at given time points. The assay may test for inhibition of O-dealkylation continuously or at specified time points.

O-Dealkylation of the compound of formula (I) following incubation with CYP3A4 gives a readily quantifiable fluorescent product of formula (II):

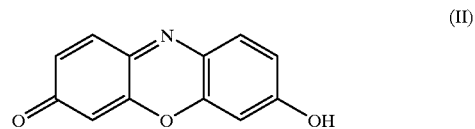

which can be scanned with suitable excitation and emission wavelengths, for example an excitation wavelength of 530 nm and an emission wavelength of 590 nm.

The assay may be carried out either in solution or utilising a solid support. When the assay is carried out in solution suitable solvents include methanol, acetonitrile and DMSO.

The test compound may be pre-incubated with enzyme prior to the addition of the substrate, or alternatively the substrate may be added simultaneously. Final concentrations of enzyme and substrate are calculated so as to achieve a suitable rate of processing for carrying out the assay. If desired, the reaction may be stopped, for example by addition of acid or solvent. The fluorescent product of formula (II) may be analysed using any conventional system of fluorescence detection, for example a multi-well plate/fluorescent plate reader.

The compound of formula (I) is novel and as such also forms part of the invention.

The compound of formula (I) may be prepared by conventional methods, for example as shown in Scheme 1:

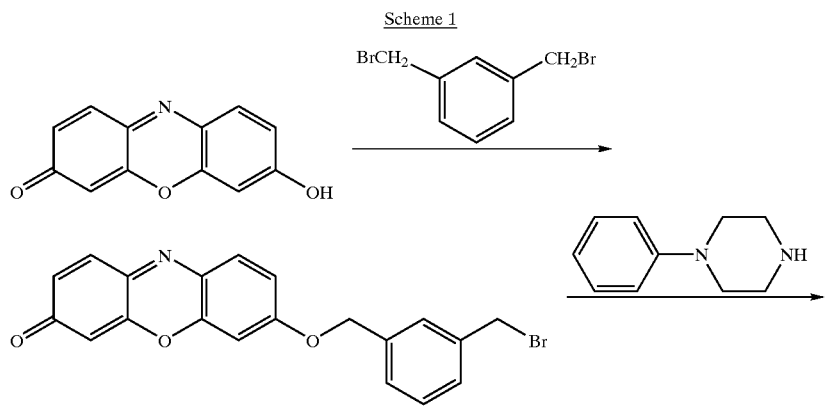

-continued

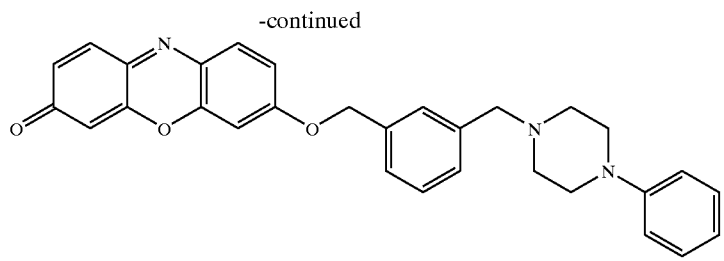

Thus according to a further aspect of the invention there is provided a process for the production of a compound of formula (I) which comprises reaction of a compound of formula (III):

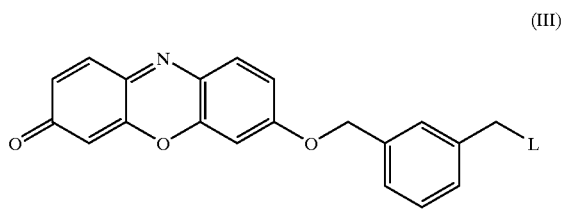

(III)

wherein L is a leaving group, e.g. Br, with 1-phenylpiperazine. The reaction is preferably performed in the presence of dimethylformamide.

The starting materials resorufin, α,α'-dibromo-m-xylene and 1-phenyl piperazine are commercially available.

Since the inhibition of cytochrome P450 enzymes is often the mechanism for drug/drug interactions, the assay according to the invention is particularly useful for identifying compounds which may give rise to adverse drug/drug interactions. The assay can therefore be used in combination with the chemical modification of test compounds to increase a test compounds potential for use as a pharmaceutical.

Thus according to further aspects of the invention there are provided a method for reducing the CYP3A4 enzyme inhibitory activity of a compound, comprising the steps of identifying the compound as an inhibitor of CYP3A4 in the assay described above; and thereafter producing a chemically modified version of the test compound in which the functionality suspected to be responsible for CYP3A4 inhibition is eliminated or changed; and novel compounds produced according to this method.

The chemical modification of test compounds according to this method can be performed using techniques well known to those skilled in the art.

The novel compounds produced according to this aspect of the invention may find application as pharmaceuticals. A compound produced according to this method will be readily identifiable as novel by performing routine literature and database searches. The pharmaceutical activity of such compounds can be readily ascertained using conventional biological screening methods known to those skilled in the art.

All publications, including but not limited to patents and patent applications, cited in this specification are herein incorporated by reference as if each individual publication were specifically and individually indicated to be incorporated by reference herein as though fully set forth.

The invention is illustrated by the following examples.

EXAMPLE 1

Preparation of resorufin 3-(4-phenylpiperazin-1-yl) methylbenzyl ether a) Resorufin 3-bromomethylbenzyl ether A mixture of resorufin (3.2 g), α,α'-dibromo-m-xylene (11.9 g), potassium carbonate (4.15 g) and dimethylformamide (90 ml) was stirred at room temperature for 3 hours. The solvent was evaporated and the residue was partitioned between dichloromethane and water. Silica gel was added to the organic phase and the solvent evaporated. Chromatography on silica gel (eluent 2% methanol in dichloromethane) gave the sub-title compound (3.0 g).

$\delta_H$(CDCl$_3$) 4.52 (s, 2H), 5.17 (s, 2H), 6.32 (d, J=2.0 Hz, 1H), 6.84 (dd, J=7.8, 2.0 Hz, 1H), 6.88 (d, J=2.7 Hz, 1H), 7.02 (dd, J=8.8, 2.7 Hz, 1H), 7.38–7.48 (m, 5H), 7.73 (d, J=8.9 Hz, 1H); mass spectrum m/z 398, 396 (MH$^+$).

b) Resorufin 3-(4-phenylpiperazin-1-yl)methylbenzyl ether

A mixture of resorufin 3-bromomethylbenzyl ether (1.0 g), 1-phenylpiperazine (1.54 ml), and dimethylformamide (50 ml) was stirred at room temperature for 2 hours. The solvent was evaporated and the residue was partitioned between dichloromethane and aqueous sodium bicarbonate solution. The organic phase was washed with water then dried (MgSO$_4$) and evaporated. The residue was purified by chromatography on silica gel (eluent 2% methanol in dichloromethane) to give the title compound (0.72 g).

$\delta_H$(CDCl$_3$) 2.60–2.63 (m, 4H), 3.18–3.20 (m, 4H), 3.60 (s, 2H), 5.18 (s, 2H), 6.32 (d, J=2.0 Hz, 1H), 6.82–7.03 (m, 6H), 7.23–7.28 (m, 2H), 7.33–7.44 (m, 5H), 7.71 (d, J=8.9 Hz, 1H); mass spectrum m/z 500 (MNa$^+$), 478 (MH$^+$).

EXAMPLE 2

Assay Methodology

Materials:
  0.5 mM resorufin 3-(4-phenylpiperazin-1-yl) methylbenzyl ether, (i.e. 0.239 mg/mL in DMSO)—store at approx. −20° C. in the dark
  2% (w/v) NaHCO$_3$—store at approx. 4° C.
  50 mM potassium phosphate buffer, pH 7.4
  Freshly prepared cofactor solution:—approx. the following per mL of 2% (w/v) NaHCO$_3$
    1.7 mg NADP, monosodium salt
    7.8 mg glucose-6-phosphate, monosodium salt
    6 Units glucose-6-phosphate dehydrogenase, Type VII from Bakers Yeast 1) Pre-warm the plate reader oven to 37° C. and pre-warm the lamp for at least 10 minutes.
2) Mix 1 μL 0.5 mM resorufin 3-(4-phenylpiperazin-1-yl) methylbenzyl ether, 5 μL (50 μg) CYP3A4 microsomal protein and 214 μL buffer per incubate (giving 2 μM resorufin 3-(4-phenylpiperazin-1-yl)methylbenzyl ether and 200 μg/mL protein final concentration).
3) To each well of a 96-well plate add 220 μL of incubation mix and 5 μL of compound (or 5 μL of appropriate solvent for control wells—methanol, acetonitrile or DMSO may be used).
4) Pre-incubate the multi-well plate in the plate reader at 37° C. for 5 minutes. Pre-warm the cofactor solution at 37° C. for 5 minutes.
5) Add 25 μL cofactor solution to each well and scan with an excitation wavelength of 530 nm and an emission wavelength of 590 nm with a gain of 80. Scan for 10 cycles at 1 minute intervals.

Results

Confirmation of resorufin 3-(4-phenylpiperazin-1-yl) methylbenzyl ether as a CYP3A4 substrate was achieved using ketoconazole, a diagnostic CYP3A4 inhibitor (Baldwin et al, *Xenobiotica*, 1995, 25, 261–270). With ketoconazole, resorufin 3-(4-phenylpiperazin-1-yl) methylbenzyl ether was inhibited with an $IC_{50}$ of 32 nM (FIG. 1), an inhibition value typical of other, well characterised, CYP3A4 substrates.

What is claimed is:
1. An assay for testing for inhibitors of the enzyme CYP3A4 which comprises contacting the enzyme and a compound of formula (I):

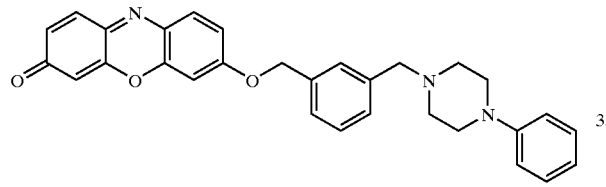

(I)

with a test compound and measuring inhibition of O-dealkylation of the compound of formula (I) by the enzyme.

2. The assay according to claim 1 wherein inhibition of O-dealkylation of the compound of formula (I) by the enzyme is measured by quantifying the compound of formula (II):

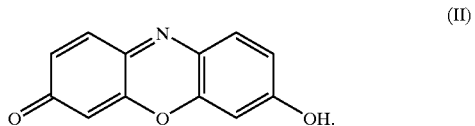

(II)

3. The assay according to claim 2 wherein the compound of formula (II) is quantified by fluorescence detection.

4. The assay according to claim 3 wherein the compound of formula (II) is quantified by scanning at excitation wavelength of 530 nm and an emission wavelength of 590 nm.

5. A compound of formula (I) as defined in claim 1.

6. A process for the production of a compound of formula (I) as defined in claim 5 which comprises reaction of a compound of formula (III):

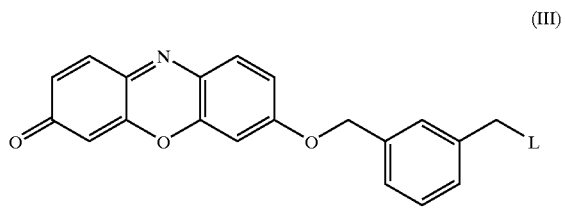

(III)

wherein L is a leaving group, with 1-phenylpiperazine.

* * * * *